United States Patent
Mestha et al.

(10) Patent No.: US 9,020,185 B2
(45) Date of Patent: Apr. 28, 2015

(54) SYSTEMS AND METHODS FOR NON-CONTACT HEART RATE SENSING

(75) Inventors: Lalit K. Mestha, Fairport, NY (US); Beilei Xu, Penfield, NY (US)

(73) Assignee: Xerox Corporation, Norwalk, CT (US)

(*) Notice: Subject to any disclaimer, the term of this patent is extended or adjusted under 35 U.S.C. 154(b) by 681 days.

(21) Appl. No.: 13/247,575

(22) Filed: Sep. 28, 2011

(65) Prior Publication Data

US 2013/0077823 A1 Mar. 28, 2013

(51) Int. Cl.
G06K 9/00 (2006.01)
A61B 5/00 (2006.01)
A61B 5/024 (2006.01)
G06K 9/20 (2006.01)

(52) U.S. Cl.
CPC .......... *A61B 5/0075* (2013.01); *A61B 5/0077* (2013.01); *A61B 5/024* (2013.01); *G06K 9/00362* (2013.01); *G06K 9/0051* (2013.01); *G06K 9/0057* (2013.01); *G06K 9/2018* (2013.01); *G06K 2009/00939* (2013.01); *A61B 5/7257* (2013.01)

(58) Field of Classification Search
None
See application file for complete search history.

(56) References Cited

U.S. PATENT DOCUMENTS

| | | | |
|---|---|---|---|
| 5,419,766 A | 5/1995 | Chang et al. | |
| 6,224,569 B1 | 5/2001 | Brimhall | |
| 2007/0024946 A1* | 2/2007 | Panasyuk et al. | 359/253 |
| 2009/0203972 A1* | 8/2009 | Heneghan et al. | 600/301 |
| 2009/0318815 A1* | 12/2009 | Barnes et al. | 600/473 |
| 2009/0326383 A1* | 12/2009 | Barnes et al. | 600/476 |
| 2011/0251493 A1* | 10/2011 | Poh et al. | 600/477 |

OTHER PUBLICATIONS

Argyros et al., "Real-Time Tracking of Multiple Skin-Colored Objects with a Possibly Moving Camera", 2004, ECCV 2004, LNCS 3023, pp. 368-379.*

Wieringa et al., Contactless Multiple Wavelength Photoplethysmographic Imaging: A First Step Toward "SpO2 Camera" Technology, Aug. 2005, Annals of Biomedical Engineering, vol. 33, No. 8 pp. 1034-1041.*

Brauers et al., Multispectral Filter-Wheel Cameras: Geometric Distortion Model and Compensation Algorithms, Dec. 2008, IEEE Transactions on Image Processing, vol. 17, No. 12.*

Kawulok, "Energy-based blob analysis for improving precision of skin segmentation". 2010, Multimedia Tools and Applications 49(3), 463-481.*

Heo et al. Performance Evaluation of Face Recognition using Visual and Thermal Imagery with Advanced Correlation Filters, 2005, Proceedings of IEEE Computer Society Conference on Computer Vision and Pattern Recognition (CVPR'05).*

(Continued)

*Primary Examiner* — Matthew Bella
*Assistant Examiner* — Jason Heidemann
(74) *Attorney, Agent, or Firm* — MH2 Technology Law Group LLP (57) ABSTRACT

An embodiment generally relates to systems and methods for estimating heart rates of individuals using non-contact imaging. A processing module can process multi-spectral video images of individuals and detect skin blobs within different images of the multi-spectral video images. The skin blobs can be converted into time series signals and processed with a band pass filter. Further, the time series signals can be processed to separate pulse signals from unnecessary signals. The heart rate of the individual can be estimated according to the resulting time series signal processing.

25 Claims, 7 Drawing Sheets

(56) References Cited

OTHER PUBLICATIONS

Poh et al. Advancements in Noncontact, Multiparameter Physiological Measurements Using a Webcam, Jan. 2011, IEEE Transactions on Biomedical Engineering, vol. 58, No. 1, pp. 7-11.*

Kraitl et al. Analysis of time series for non-invasive characterization of blood components and circulation patterns, 2008, Nonlinear Analysis: Hybrid Systems, Elsevier, vol. 2 pp. 441-455.*

Perry et al., Non-Contact Vital Sign Monitoring via Ultra-Wideband Radar, Infrared Video, and Remote Photoplethysmography: Viable Options for Space Exploration Missions, May 2011, NASA, pp. 1-8.*

Jakovels et al., RGB Imaging System for Mapping and Monitoring of Hemoglobin Distribution in Skin, 2011, SPIE vol. 8158, pp. 1-6.*

Bhowmik et al. Chapter 6: "Thermal Infrared Face Recognition—A Biometric Identification Technique for Robust Security system" in: Reviews, Refinements and New Ideas in Face Recognition, (Jul. 27, 2011), pp. 113-138, ISBN: 978-953-307-368-2.*

Xu, Beilei, Lalit Keshav Mestha, Yao Rong Wang and Peter Paul, "A Multi-Layer Array for a Multi-Resolution Multi-Spectral Camera," U.S. Appl. No. 13/239,642, filed Sep. 22, 2011.

Yang, Ming, Qiong Liu, Thea Turner and Ying Wu, "Vital Sign Estimation from Passive Thermal Video," IEEE Conference on Computer Vision and Pattern Recognition, Jun. 2008, pp. 23-28.

Garbey, Marc, Nanfei Sun, Arcangelo Meria and Ioannis Pavildis, "Contact-Free Measurement of Cardiac Pulse Based on the Analysis of Thermal Imagery," IEEE Transactions on Biomedical Engineering, Aug. 2007, vol. 54, No. 8, pp. 2-13.

Mestha, Lalit Keshav, Beilei Xu and Peter Paul, "Method for Classifying a Pixel of a Hyperspectral Image in a Remote Sensing Application," U.S. Appl. No. 13/023,310, filed Feb. 8, 2011.

Wang, Yao Rang, Zhigang Fan and Lalit Keshav Mesta, "Determining a Total Number of People in a IR Image Obtained Via an IR Imaging System," U.S. Appl. No. 12/967,775, filed Dec. 14, 2010.

Xu, Beilei, Whencheng Wu, Lalit Keshav Mestha and Graham Pennington, "System and Method for Object Identification and Tracking," U.S. Appl. No. 13/247,343, filed Sep. 28, 2011.

Lee, Jong-Hwan, Ho-Young Jung, Te-Won Lee and Soo-Young Lee, "Speech Coding and Noise Reduction Using Ice-Based Speech Features," in P. Pajunen and J. Karhunen (eds.), Proc. Second International Workshop on Independent Component and Analysis and Blind Signal Separation, 2000.

Hoyer, Patrik O. and Aapo Hyvärinen, "ICA Features of Colour and Stereo Images," P. Pajunen and J. Karhunen (eds.), Proc. Second International Workshop on Independent Component and Analysis and Blind Signal Separation, 2000, pp. 567-572.

Bell, Anthony J and Terrence J. Sejnowski, "The "Independent Components" of Natural Science are Edge Filters," Vision Ref., 1997, vol. 37, No. 23, pp. 3327-3338.

Lee, Su-In and Serafim Batzoglou, "Application of independent component analysis to microarrays," Genome Biology, 2003, vol. 4. Issue 11, R76.

Cantelli, Mark, "Are you in There?" TOLLTRANS 2011, www.TrafficTechnologyToday.com.

Wei Lu et al., "Approach and Applications of Constrained ICA", IEEE Transactions on Neural Networks, vol. 16, No. 1, Jan. 2005.

Wei Lu, et al., "Constrained Independent Component Analysis", School of Computer Engineering, Nanyang Technological University, Singapore 636798, 2001.

Takano, et al., "Heart rate measurement based on a time-lapse image", Medical Engineering & Physics 29 (2007), pp. 853-857, www.sciencedirect.com.

Poh, et al., "Non-contact, automated cardiac pulse measurements using video imaging and blind source separation," May 10, 2010, vol. 18, No. 10 / OPTICS EXPRESS 10762.

J. Lee, at al "Temporally constrained ICA-based foetal ECG separation", Electronics Letters, Oct. 13, 2005, vol. 41, No. 21.

* cited by examiner

SYSTEMS AND METHODS FOR NON-CONTACT HEART RATE SENSING

FIELD OF THE INVENTION

This invention relates generally to imaging systems and, more particularly, to systems and methods for non-contact sensing of heart rate.

BACKGROUND OF THE INVENTION

Use of imaging in healthcare, law enforcement, surveillance, and other fields, can be beneficial because it can lead to solutions in identification, analysis, and diagnosis techniques related to the fields. Further, pulse or heart rate monitoring techniques such as electrocardiography (ECG) are used to interpret electrical activity of a heart over a period of time. In particular, when the heart muscle depolarizes during each heartbeat, the ECG device can detect and amplify resulting electrical changes on the skin. Electrodes are affixed to the skin of the subject via conducting gel embedded in the middle of an adhesive pad onto which cables clip. The recording that is produced, from the ECG amplification is referred to as an electrocardiogram.

Current ECG systems and techniques require the patient to be located locally to the ECG machine. In particular, the patient needs to affix the electrodes to his or her skin. However, the adhesive electrodes can cause skin irritation, discomfort, and other issues to the patient. This can especially be a problem in neonatal intensive care units (ICU), as newborns skin can be especially sensitive.

Therefore, it may be desirable to have systems and methods for non-contact cardiac pulse measurement. In particular, it may be desirable to use non-contact imaging in systems and methods for automated in-hospital and/or in-home monitoring.

SUMMARY

An embodiment pertains generally to a method of processing data. The method comprises processing a multi-spectral video of an individual. The processing comprises separating the multi-spectral video into a sequence of image data cubes comprising a set of entries, wherein each entry of the set, of entries corresponds to a spectral frequency at which the multi-spectral video was captured. Further, the processing comprises identifying, from the image data cubes, a set of skin blobs corresponding to the set of entries; generating, from the set of skin blobs, a set of time series signals; processing the set of time series signals to estimate a heart rate of the individual; and providing the heart rate to a device.

Another embodiment pertains generally to a system for processing data. The system comprises a one or more filters configured to filter images of an individual into multi-spectral images. Further, the system comprises a capture device configured to capture, from the one or more filters, the multi-spectral images as a multi-spectral video. Still further, the system comprises a processor coupled to the capture device and configured to process the multi-spectral video. The processing comprises separating the multi-spectral video into a sequence of image data cubes comprising a set of entries, wherein each entry of the set of entries corresponds to a spectral frequency at which the multi-spectral video was captured. Further, the processing comprises identifying, from the image data cubes, a set of skin blobs corresponding to the set of entries; generating, from the set of skin blobs, a set of time series signals; processing the set of time series signals to estimate a heart rate of the individual; and providing the heart rate to a device.

BRIEF DESCRIPTION OF THE DRAWINGS

Various features of the embodiments can be more fully appreciated, as the same become better understood with reference to the following detailed description of the embodiments when considered in connection with the accompanying figures, in which.

DESCRIPTION OF THE EMBODIMENTS

Reference will now be made in detail to the present embodiments (exemplary embodiments) of the invention, examples of which are illustrated in the accompanying drawings. Wherever possible, the same reference numbers will be used throughout the drawings to refer to the same or like parts. In the following description, reference is made to the accompanying drawings that form a part thereof, and in which is shown by way of illustration specific exemplary embodiments by which the invention may be practiced. These embodiments are described in sufficient detail to enable those skilled in the art to practice the invention and it is to be understood that other embodiments may be utilized and that changes may be made without departing from the scope of the invention. The following description is, therefore, merely exemplary.

While the invention has been illustrated with respect to one or more implementations, alterations and/or modifications can be made, to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising." The term "at least one of" is used to mean one or more of the listed items can be selected.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume values as defined earlier plus negative values, e.g. −1, −1.2, −1.89, −2, −2.5, −3, −10, −20, −30, etc.

Embodiments as described herein generally relate to systems and methods for non-contact heart rate estimation. In particular, the systems and methods can comprise video-based infrared imaging technology to provide contact-free heart rate estimating and monitoring. According to embodiments, multi-spectral, remote, skin-detection technology can be used to detect and extract exposed skin areas from individuals. Further, average pixel values from exposed skin areas can be converted to a zero-mean unit variance signal at a corresponding time. A time history of signals can be recorded over a pre-defined period of time, and the time history signals can be prefiltered and processed to separate an underlying pulsing signal by, for example, using an independent component analysis (ICA) algorithm when multiple bands are used during video and image capture. Finally, the separated pulsing signal from the algorithm can be transformed into frequency spacing data using a Fast Fourier Transform (FFT), in which the heart rate can be extracted or estimated.

The heart rate estimating systems and methods as described herein can be used to create platform technology for automated monitoring of patients of all ages via non-invasive and non-contact video images taken from cameras and other image and video capture devices. Further, the platform technology can be applicable to solutions and services related to in-hospital services (e.g. ICU and/or triage), in-home monitoring of individuals (e.g. elderly individuals, newborns, etc.), and treatment of hospitalized patients requiring supervision. It should be understood that the systems, methods, and techniques as described herein can be extended or otherwise implemented in other fields such as, for example, pet and animal monitoring, airport control, border crossings, traffic enforcement, surveillance, and other services.

As the human heart pumps blood, cardiovascular pulse waves can propagate throughout the body. Further, during the cardiac cycle, slight changes can occur in blood vessels present underneath the skin. By recording video or images of the region of skin where concentrations of blood vessels exist, small changes in blood vessels can register as reflected signals on detector arrays. The reflected signals can comprise a mixture of reflected plethysmographic signals, along with other artifacts. Further, apart from the cardiac pulse, the detector arrays can also register involuntary and voluntary bodily motions and fluctuations due to, for example, ambient illumination. Various signal processing algorithms and techniques can be used to separate signals from independent sources.

According to embodiments, the systems and methods as described herein can utilize multi-band skin detection technology in a wavelength range of, for example, 700 nanometers (nm) to 1700 nm. Human skin can, reflect certain wavelengths of light differently than reflections by fabric polymers or other types of materials. Therefore, by capturing image data cube at multiple wavelengths simultaneously, analysis techniques can accurately classify skin objects even through, for example, a glass windshield, an oxygen mask placed over a patient's face, and other objects that can be reasonably transparent to infrared wavelengths. Further, the multiband image processing techniques can be used to detect skin blobs within a wavelength band of interest, and process the skin blobs to estimate heart rates of the individuals. In embodiments, the wavelengths can be chosen anywhere between 400 nm to 2400 nm to accomplish skin detection and signal separation, and to estimate heart rate.

Figure 1:
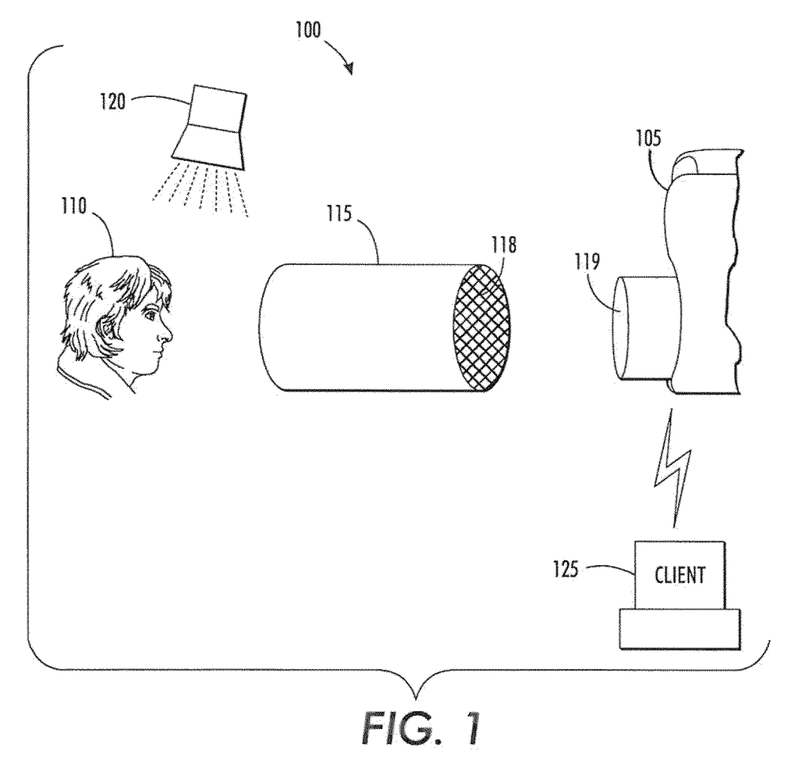
FIG. 1 illustrates an exemplary environment depicting an image capture device and associated components, in accordance with embodiments.

According to embodiments, the systems and methods comprise functionality to capture multi-spectral video images of individuals. As shown in FIG. 1, depicted is an exemplary environment 100 configured to capture multi-spectral images of individuals. The environment 100 can comprise a capture device 105 such as, for example, a video camera or other imaging device, that can be used to capture images at varying wavelength bands. For example, as shown in FIG. 1, the capture device 105 be configured to capture images of an individual 110 that can be positioned in front of the capture device 105. The capture device 105 can be a multi-spectral video camera, a multi-spectral Near Infrared video camera, a multi-spectral Short Wave Infrared video camera, a red-green-blue (RGB) video camera, or other cameras. In embodiments, a lens-filter combination 115, 118, such as a normal lens structure and a filter grid with different filter material to accomplish, multi-spectral imaging capability for simultaneous capture, can be positioned along the optical axis of the capture device 105, and can be used to filter the image of the individual 110 before receipt by the capture device 105. It should be envisioned that other configurations and positionings of the capture device 105, lens-filter combination 115, 118, and individual 110 are envisioned.

In embodiments, the multiple filter grid 118 can be assembled on a detector array of the capture device 105. The lens-filter combination 115, 118 can be reversed with the filter 118 being placed before the lens 115 along the optical axis of the lens 115 and the lens 115 positioned close to the capture device 105. Also a lens 119 on the capture device 105 could be a honeycomb lens with a multiple filter grid that can be directly mounted in front of the capture device 105 such as, for example, the type designed using the Fabry-Perot method. The honeycomb lens structure, when positioned on the capture device 105 along the optical axis past the multiple filter grid 118, can direct the dispersed light components onto a 2D detector array in the capture device 105. Further, the lens-filter combination 115, 118 can be implemented as the capture device itself with a multiple filter grid and honeycomb lens providing an optical path and a desired transmission of wavelengths on to the detector array.

According to embodiments, each grid on the multiple filter grid 118 can be tuned to filter the incoming image at a specified wavelength. For example, one filter on the grid can filter the image at 800 nm, another one at 850 nm, another one at 900 nm, another one at 1000 nm, another one at 1450 nm, and so on. Further, one group can be targeted for pulse detection and another group for skin detection, and so on. It should be appreciated that various combinations of the number of filters in the grid and the filter wavelengths of the grids are envisioned, and can be assembled based on the need. Further, it should be appreciated that other filtering components and elements to capture multi-spectral images are envisioned. Still further, the wavelengths of the grid can be set or adjusted to capture light from various ranges such as infrared, visible, ultraviolet, and other ranges. In embodiments, the multiple filter grid 118 can be tunable or of a fixed wavelength, whereby the tunability can be obtained by, for example, actuating a gap between a Fabry-Perot interferometer, or adjusting other devices or controls of the multiple filter grid 118 and/or other components. In other embodiments, an illuminator 120 or similar device can be used to provide enough illumination in the infrared wavelength band of the capture device 105.

As shown in FIG. 1, the environment can further comprise a client 125 that can comprise components and elements that can perform functions and execute applications related to the processing of imaging data and other data. The client 125 can be connected to the capture device 105 via a wired or wireless connection. In embodiments, a computer or similar storage device with image data can be connected to the client 125. It should be appreciated that other data access and transfer techniques are envisioned. In embodiments, the client 125 can be configured with any necessary hardware or software to process the image, data in accordance with the functionality as described herein.

Figure 2A:
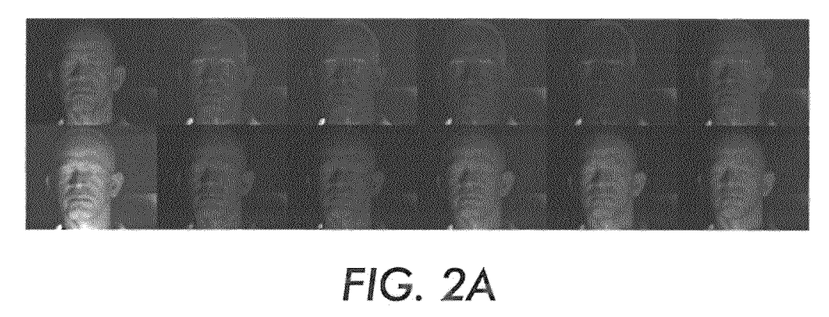
FIG. 2A illustrates an exemplary image cube, in accordance with embodiments.

According to embodiments, the capture device 105 can be configured to capture two-dimensional video images of the individual 110. In embodiments, the capture device 105 can capture different views of the individual 110 such as, for example, side views, front views, infants views (i.e. sleep poses), and other views. The capture device 105, or other processing applications or devices, can decompose a captured image into its spectral bands to form a data cube. For example, FIG. 2A depicts an exemplary data cube depicting 12 images at 12 different wavelength bands ranging from 1000 nm to 1660 nm. As shown in FIG. 2A, the different images can have different contrast levels and other features, based on the wavelength bands, and the filter transmission efficiency and detector quantum efficiency at the band.

Figure 2B:
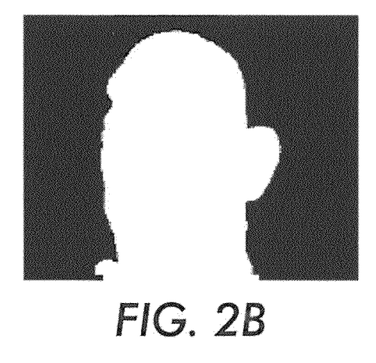
FIG. 2B illustrates an exemplary processed image, component, in accordance with embodiments.

In embodiments, the data cube images can be used to identify skin blobs of the individual(s) depicted in the images. In particular, the data cube images can be processed to produce "skin blobs" using, for example, data driven approaches, physics-based models, blob analyses, and other techniques. In addition, post-processing techniques can be implemented to filter out sporadic false-positive pixels often present in classified results, and other outputs. Further, connected component analyses and other techniques can be performed on the images to form dense skin blobs within the skin areas as shown, for example, in FIG. 2B. In some embodiments, a face tracking algorithm can be used to constrain the region of interest to the face region, and then a skin blob processing technique can be used to retain only skin area.

In embodiments, the pixels within the skin blobs across each wavelength channel or wavelength channel of interest in the data cube can be processed to generate time series signals. In particular, the data cube can comprise one or more channels per frame between infrared wavelengths in a range of, for example, 680 nm to 1000 nm, or other values within an optimal medical spectral window. For example, in a video of length 1 minute, and with a 30 frame per second capture speed, there will be 1800 resulting frames to analyze. In embodiments, a frame can refer to a data cube at a given time. In embodiments, an average of all pixels in a skin blob region can be computed across each spectral channel within the frame, resulting in a channel-by-channel average for the frame. Further, in embodiments, a global channel average corresponding to the selected channel can be computed by adding averages of the selected channel from multiple frames and dividing by the total number of frames. In addition, the channel average of each frame can be subtracted by the global channel average and the resulting signal can be divided by a global channel standard deviation, which can result in a zero-mean unit variance time series signal. In embodiments, the channels that can be used for estimating heart rate may not be the same as the channels used for extracting skin blobs, since wavelengths of the respective channels could be different. The time series signals can contain frequency components related to heart rate as well as frequencies related to other motion and breathing artifacts. Further, any ambient illumination used on the capture device can lead to fluctuation at a higher beat frequency. Therefore, prior to performing a heart rate extraction, it can be useful to prefilter the channel-based signals by using a band pass filter to limit the frequency ranges. In particular, the band pass filter can remove undesirable frequencies below and above the expected heart rate frequencies. As a point of reference, a normal resting heart rate for an adult is 60 to 100 beats per minute (bpm), and an infant can have a heart rate of 70-170 bpm. Therefore, the band pass filter can be configured to filter out artifacts below the lower range and above the upper range. It should be appreciated that a heart rate for an individual can vary outside of these exemplary ranges.

Figure 3A:
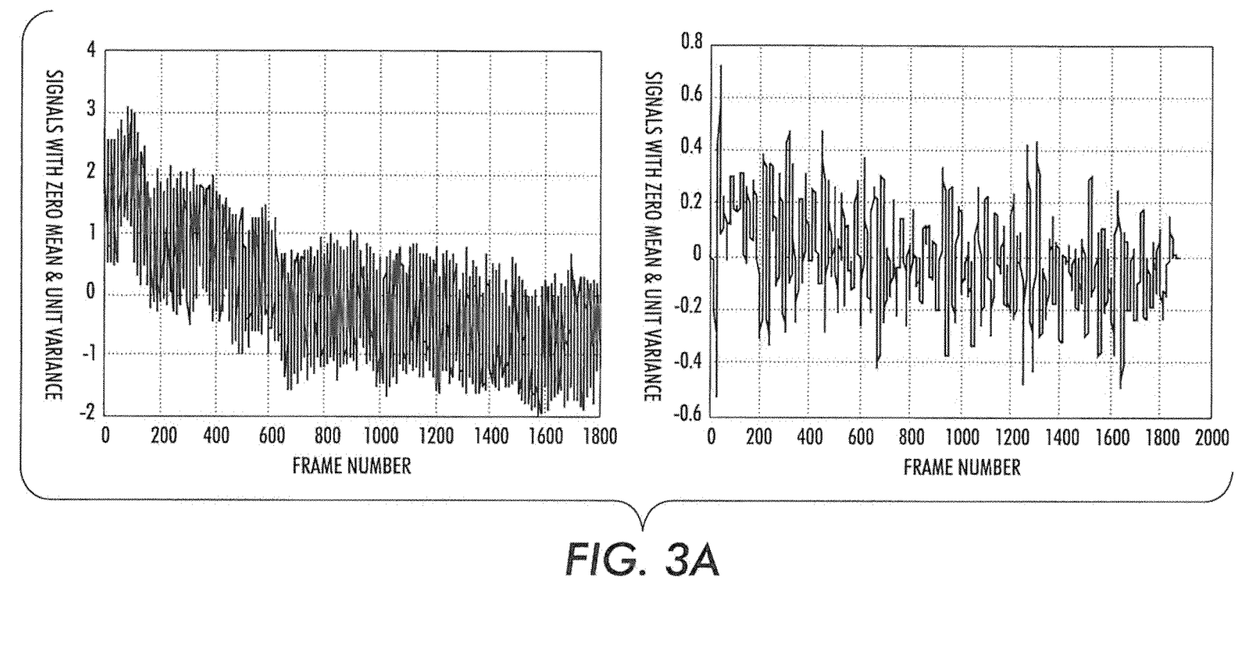
FIG. 3A is an exemplary image processing output, in accordance with embodiments.
Figure 3B:
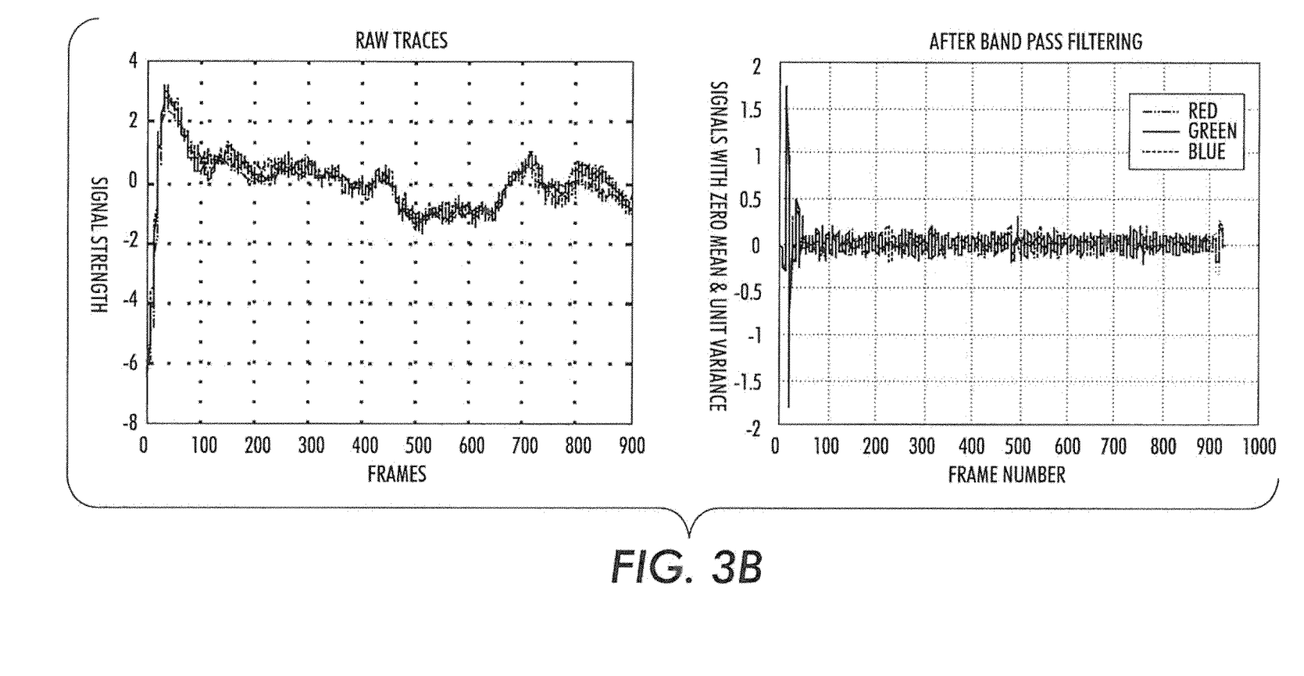
FIG. 3B is an exemplary image processing output, in accordance with embodiments.

Referring to FIGS. 3A and 3B, depicted are time series signals before and after band pass filtering. In particular, FIG. 3A depicts a time series signal that was captured with a 800 nm filter on an infrared camera, and FIG. 3B depicts a time series signal for three color channels that was captured with a red-green-blue (RGB) video camera. Further, the time series signal of FIG. 3A was taken from a 1 minute long video at 30 frames per second, and the bandwidth for the band pass filter was 30 to 120 bpm. The time series signal of FIG. 3B was taken from a 1 minute video at 15 frames per second, and the bandwidth for the band pass filter was 48 to 120 bpm. Further, a higher order limited finite impulse response (FIR) filter was used to constrain the band width. As shown in FIGS. 3A and 3B, the traces on the left depict the time series signal prior to the band pass filtering, and the traces on the right depict the time series signal after the band pass filtering. More particularly, the band pass filtering results as shown in FIGS. 3A and 3B show that the band pass filter can be effective in filtering out artifacts and frequencies below and above the expected frequency ranges.

In embodiments, an independent component analysis (ICA) can be performed on the data to separate source or pulse signals from motion and other unnecessary signals. More particularly, the ICA is a statistical decomposition technique that can be used to extract useful information from data in a variety of domains such as, for example, speech signal processing, natural color image representation, neuroscience, genomics, and other domains. In embodiments, the ICA can look for statistically independent factors, causes, sources, and the like, in data, as opposed to uncorrelated factors. Specifically, given a stream of data $x_1, x_2, \ldots, x_n$, where each $x_i$ can be a vector of length n; the stream can be represented as a random sample from a mixture model as specified by equation (1):

$$x(t)=As(t) \qquad (1)$$

As specified in equation (1), A can correspond to the mixture matrix with dimensions n×r, and s can correspond to a vector of length r with a property that the component random variables $s_1, s_2, \ldots, s_r$, are statistically independent sources. Further, the columns of A, denoted by $a_1, a_2, \ldots, a_r$ can be basis, vectors. In particular, a basis can be constructed from the signal data such that the underlying source signals s can be made up of statistically independent components. In embodiments, it can be assumed that r=n and that searching for an optimal A can be equivalent to searching for an optimal W ("de-mixing matrix"), wherein W is the inverse of A. Further, the assumption that r=n can be relaxed depending on a number of channels present and/or a number of independent sources to extract.

In embodiments, in RGB video images, there can be three channels ($x_1$, $x_2$, $x_3$) that can be used to construct the de-mixing matrix W. In other, embodiments, in a multispectral infrared camera, there can be many channels. Further, the independent components ($s_1$, $s_2$, $s_3$) can be estimated using the de-mixing matrix W as specified by equation (2):

$$s_{hat}(t)=Wx(t) \qquad (2)$$

According to embodiments, once the estimated source signals $s_{hat(t)}$ have been isolated or otherwise located, the estimated source signals can be used to estimate the heart rate of the individual. In particular, the heart rate can be extracted by performing additional signal processing on the source separated signals as specified by equation (2). In particular, a power spectrum can be obtained by applying the Fast Fourier Transform (FFT) on the selected source signal. For example, the green channel can be selected for RGB video images because, the green channel is inherently rich in capturing change in volumetric blood signature. In embodiments, the magnitudes of the FFT can be squared, and the pulse or heart rate frequency at which the peak occurs can be extracted. The peak pulse frequency can be used as the estimation for the heart rate of the individual.

Figure 4A:
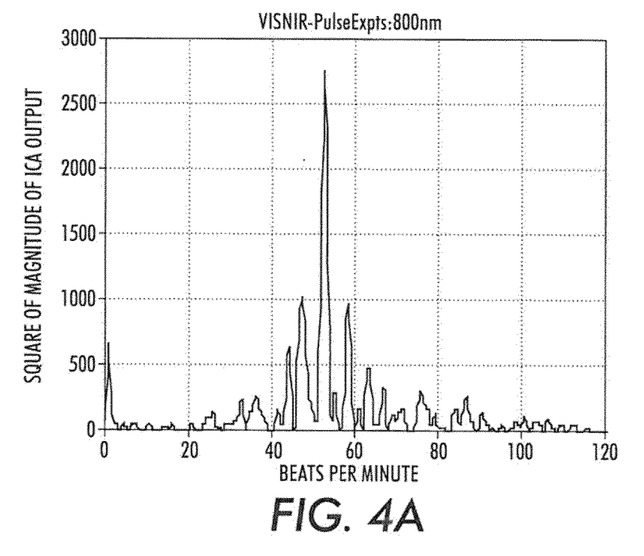
FIG. 4A is an exemplary image, processing output, in accordance with embodiments.
Figure 4B:
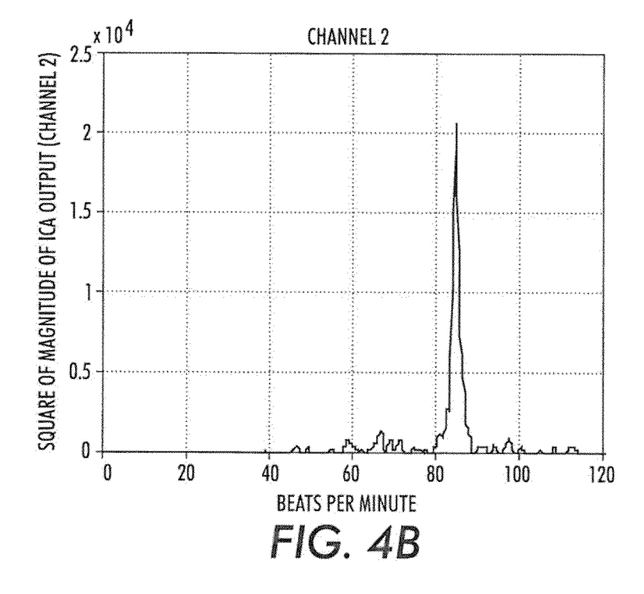
FIG. 4B is an exemplary image processing output, in accordance with embodiments.

FIGS. 4A and 4B depict outputs resulting from squaring the magnitudes of the FFT. In particular, the pulse frequency corresponds to the highest power of the square of the magnitude spectrum within the range of interest. In FIG. 4A, the time signal with respect to an individual's heart rate for an 800 nm image captured about 5 meters away from the first individual's face was processed with a FFT, and the magnitude was squared. As an output, the heart rate of the first individual, as depicted in FIG. 4A, is estimated as 52.7 beats/minute. Further; as shown in FIG. 4B, the time signal with respect to a second individual's heart rate for an RGB image captured about 0.5 meters away from the second individual's face was processed with ICA, and the magnitude was squared. As an output, the heart rate of the second individual, as depicted in of FIG. 4B, is estimated as 84.4 beats/minute. In embodiments, simultaneous capture in different wavelengths within an IR band can allow for greater robustness. In particular, the simultaneous capture allows for all spectral bands to be captured and processed simultaneously to separate the independent sources, and then select the one that contains a dominant signal.

Figure 5:
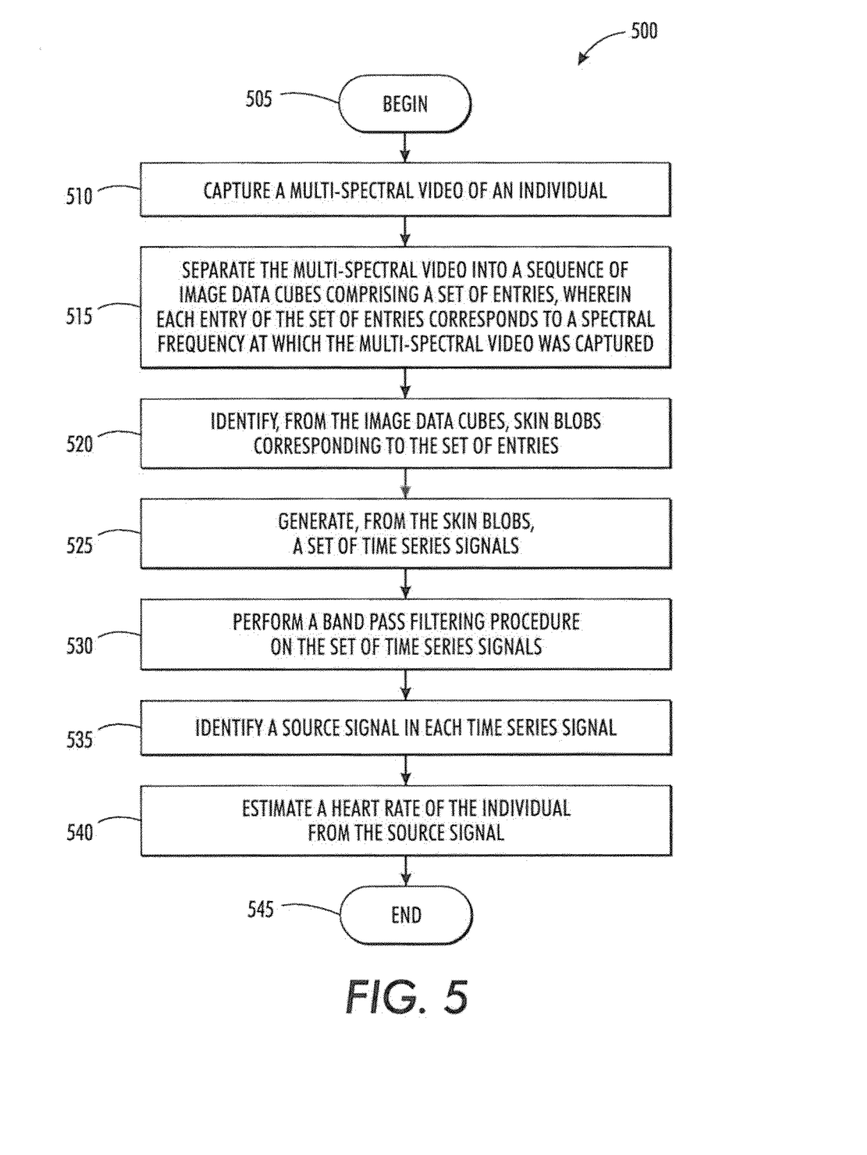
FIG. 5 illustrates an exemplary flow diagram of processing data in accordance with another embodiment.

Referring to FIG. 5, depicted is a flowchart detailing a non-invasive technique 500 used to estimate a heartbeat of an individual. It should be readily apparent to those of ordinary skill in the art that the flow diagram depicted in FIG. 5 represents a generalized illustration and that other steps can be added or existing steps can be removed or modified.

In 505, processing can begin. In 510, a multi-spectral video of an individual can be captured. In embodiments, the multi-spectral video can comprise multiple wavelength bands ranging from, for example, 700 nm to 1700 nm. In 515, the multi-spectral video can be separated into a sequence of image data cubes comprising a set of entries, wherein each entry of the set of entries corresponds to a spectral frequency at which the multi-spectral image was captured. For example, the image data cube can comprise twelve (12) entries, with each entry corresponding to images captured at each of the 12 different wavelength bands. In embodiments, the each entry can further correspond to a time at which the multi-spectral image was captured.

In 520, skin blobs corresponding to the set of entries can be identified from the image data cube. In embodiments, the skin blobs can be identified using data driven approaches, physics-based models, blob analyses, and other techniques. The skin blobs can be identified from each frame independently or identified using the first frame and tracked from frame-to-frame using a conventional video tracking method. In 525, a set of time series signals can be, generated from the sequence of skin blobs from the video. In embodiments, the set of time series signals can be calculated using frame averages, a global average, and a global standard deviation. In 530, a band pass filtering procedure can be performed on the set of time series signals. In embodiments, a frequency of the band pass filtering procedure can be selected based on an age, health level, and other factors, that relate to the individual.

In 535, a source signal can be identified in each time series signal, subsequent to the band pass filtering. In embodiments, an independent component analysis (ICA) can be performed on the time series signals to separate independent source signals. In other embodiments, an analysis can be performed on RGB images to identify the source signals. In 540, a heart rate of the individual can be estimated from the estimated source signal. In embodiments, the heart rate can be estimated by applying a Fast Fourier Transform on the estimated source signal, squaring the magnitude, and then extracting the heart rate at which the peak occurs. In 545, processing can end, repeat, or return to any of the previous steps.

Figure 6:
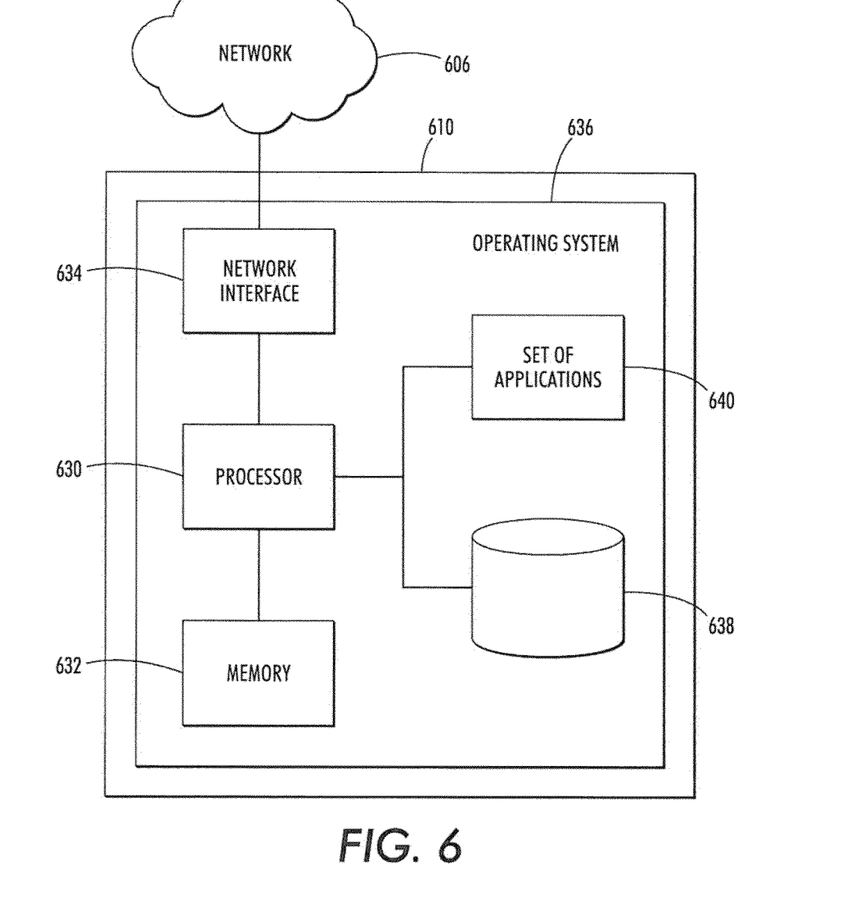
FIG. 6 illustrates a hardware diagram in accordance with another embodiment.

FIG. 6 illustrates an exemplary diagram of hardware and other resources that can be incorporated with processing and logic associated with the present embodiments. As shown in FIG. 6, a server 610 can be configured to communicate with a network 606. In embodiments as shown, the server 610 can comprise a processor 630 communicating with memory 632, such as electronic random access memory, or other forms of transitory or non-transitory computer readable storage mediums, operating under control of or in conjunction with an operating system 636. The operating system 636 can be any commercial, open-source, or proprietary operating system or platform. The processor 630 can communicate with a database 638, such as a database stored on a local hard drive. While illustrated as a local database in the server 610, the database 638 can be separate from the server 610.

The processor 630 can further communicate with a network interface 634, such as an Ethernet or wireless data connection, which in turn communicates with the network 606, such as the Internet or other public or private networks. The processor 630 can also communicate with the database 638 or any applications 640, such as applications associated with the client 125, to execute control logic and perform data processing, as described herein.

While FIG. 6 illustrates the server 610 as a standalone system comprising a combination of hardware and software, the server 610 can also be implemented as a software application or program capable of being executed by a conventional computer platform. For example, it should be understood that the components of the server 610 can be implemented on user PCs or other hardware such that the user PCs can communicate directly with the database 638. Likewise, the server 610 can also be implemented as a software module or program module capable of being incorporated in other software applications and programs. In either case, the server 610 can be implemented in any type of conventional proprietary or open-source computer language.

Certain embodiments can be performed as a computer program. The computer program can exist in a variety of forms both active and inactive. For example, the computer program can exist as software program(s) comprised of program instructions in source code, object code, executable code or other formats; firmware program(s); or hardware description language (HDL) files. Any of the above can be embodied on a transitory or non-transitory computer readable medium, which include storage devices and signals, in compressed or uncompressed form. Exemplary computer readable storage devices include conventional computer system RAM (random access memory), ROM (read-only memory), EPROM (erasable, programmable ROM), EEPROM (electrically erasable, programmable ROM), and magnetic or optical disks or tapes. Exemplary computer readable signals, whether modulated using a carrier or not, are signals that a computer system hosting or running the present invention can be configured to access, including signals downloaded through the Internet or other networks. Concrete examples of the foregoing include distribution of executable software program(s) of the computer program on a CD-ROM or via Internet download. In a sense, the Internet itself, as an abstract entity, is a computer readable medium. The same is true of computer networks in general.

While the invention has been described with reference to the exemplary embodiments thereof, those skilled in the art will be able to make various modifications to the described embodiments without departing from the true spirit and scope. The terms and descriptions used herein are set forth by way of illustration only and are not meant as limitations. In particular, although the method has been described by examples, the steps of the method can be performed in a different order than illustrated or simultaneously. Those skilled in the art will recognize that these and other variations are possible within the spirit and scope as defined in the following claims and their equivalents.

What is claimed is:

1. A method of processing data, the method comprising:
   processing, by a processor, a video of an individual, wherein the video was captured using one or more of a multi-spectral video camera, a multi-spectral near infrared video camera, or a multi-spectral short wave Infrared video camera, and wherein the processing comprises:
      separating the video into a sequence of image data cubes each comprising a set of more than three entries, wherein each entry of each set of entries corresponds to a spectral frequency at which the video was captured, wherein the spectral frequency of each entry of the set of entries is in a range of 700 nanometers (nm) to 1700 nm;
      identifying, from the image data cubes, a set of skin blobs corresponding to the set of entries;
      processing the set of skin blobs to remove non-skin areas;
      generating, from the set of skin blobs, a set of time series signals;
      processing the set of time series signals to estimate a heart rate of the individual; and
      providing the heart rate to a device.

2. The method of claim 1, wherein the processing further comprises:
   processing the set of time series signals to identify a source signal that corresponds to a heart beat.

3. The method of claim 1, wherein identifying the set of skin blobs comprises:
   identifying the set of skin blobs from a first frame of the image data cubes; and
   tracking the set of skin blobs in successive frames of the image data cubes using motion-based video tracking.

4. The method of claim 1, wherein the processing further comprises:
   processing the set of time series signals to separate independent source signals that contain a heart beat.

5. The method of claim 1, further comprising:
   capturing the video.

6. The method of claim 1, wherein the processing further comprises:
   processing the sequence of image data cubes to estimate the heart rate on a continuous basis.

7. The method of claim 1, wherein the processing further comprises:
   prefiltering the set of time series signals by a band pass filter.

8. The method of claim 1, wherein generating the set of time series signals comprises:
   computing a channel average of pixels in each skin blob of the set of skin blobs;
   computing a global channel average based on the channel average of pixels in each skin blob; and
   generating the set of time series signals by subtracting the global channel average from the channel average of pixels, and dividing a result of the subtraction by a global channel standard deviation.

9. The method of claim 1, wherein processing the set of time series signals comprises performing an independent component analysis (ICA) on the set of time series signals.

10. The method of claim 1, wherein estimating the heart rate of the individual comprises:
    applying a Fast Fourier Transform (FFT) on a source signal from the set of time series signals to generate an FFT source signal; and
    calculating a square of the FFT source signal; and
    estimating the heart rate of the individual based on the calculation of the square of the FFT source signal.

11. The method of claim 10, wherein estimating the heart rate of the individual based on the calculation of the square of the FFT source signal comprises:
    identifying a greatest magnitude of the square of the FFT source signal within a frequency band of interest.

12. The method of claim 1, wherein providing the heart rate to the device comprises:
    outputting the heart rate of the individual to a display monitor.

13. The method of claim 1, wherein the processing further comprises:
    outputting a source signal used to estimate the heart rate on a display monitor.

14. A system for processing data, the system comprising:
    one or more filters configured to filter images of an individual into multi-spectral images;
    a capture device configured to capture, from the one or more filters, the multi-spectral images as a video, wherein the capture device comprises one or more of a multi-spectral video camera, a multi-spectral near infrared video camera, or a multi-spectral short wave Infrared video camera; and
    a processor coupled to the capture device and configured to perform actions comprising:
       processing the video, wherein the processing comprises:
          separating the video into a sequence of image data cubes each comprising a set of more than three entries, wherein each entry of each set of entries corresponds to a spectral frequency at which the multi-spectral video was captured, wherein the spectral frequency of each entry of the set of entries is in a range of 700 nanometers (nm) to 1700 nm;
          identifying, from the image data cubes, a set of skin blobs corresponding to the set of entries;

processing the set of skin blobs to remove non-skin areas;
generating, from the set of skin blobs, a set of time series signals;
processing the set of time series signals to estimate a heart rate of the individual; and
providing the heart rate to a device.

15. The system of claim 14, wherein identifying the set of skin blobs comprises:
identifying the set of skin blobs from a first frame of the image data cubes; and
tracking the set of skin blobs in successive frames of the image data cubes using motion-based video tracking.

16. The system of claim 14, wherein the processing further comprises:
processing the set of time series signals to identify a source signal that corresponds to a heart beat.

17. The system of claim 14, wherein the processing further comprises:
processing the set of time series signals to separate independent source signals that contain a heart beat.

18. The system of claim 14, wherein the processing further comprises:
processing the sequence of image data cubes to estimate the heart rate on a continuous basis.

19. The system of claim 14, wherein the processing further comprises:
prefiltering the set of time series signals by a band pass filter.

20. The system of claim 14, wherein generating the set of time series signals comprises:
computing a channel average of pixels in each skin blob of the set of skin blobs;
computing a global channel average based on the channel average of pixels in each skin blob; and
generating the set of time series signals by subtracting the global channel average from the channel average of pixels, and dividing a result of the subtraction by a global channel standard deviation.

21. The system of claim 14, wherein processing the set of time series signals comprises performing an independent component analysis (ICA) on the set of time series signals.

22. The system of claim 14, wherein estimating the heart rate of the individual comprises:
applying a Fast Fourier Transform (FFT) on a source signal from the set of time series signals to generate an FFT source signal; and
calculating a square of the FFT source signal; and
estimating the heart rate of the individual based on the calculation of the square of the FFT source signal.

23. The system of claim 22, wherein estimating the heart rate of the individual based on the calculation of the square of the FFT source signal comprises:
identifying a greatest magnitude of the square of the FFT source signal within a frequency band of interest.

24. The system of claim 14, wherein providing the heart rate to the device comprises:
outputting the heart rate of the individual to a display monitor.

25. The system of claim 14, wherein the processing further comprises:
outputting a source signal used to estimate the heart rate on a display monitor.

* * * * *